United States Patent [19]

Bridger et al.

[11] 4,130,496
[45] Dec. 19, 1978

[54] PROCESS OF PREPARING MONOARYL PHOSPHONATES AND LUBRICANT COMPOSITIONS CONTAINING SAME

[75] Inventors: Robert F. Bridger, Hopewell; Kirk D. Schmitt, Pennington, both of N.J.

[73] Assignee: Mobil Oil Corporation, New York, N.Y.

[21] Appl. No.: 867,850

[22] Filed: Jan. 9, 1978

Related U.S. Application Data

[62] Division of Ser. No. 717,815, Aug. 26, 1976, Pat. No. 4,092,254.

[51] Int. Cl.$^2$ ............................................... C10M 1/10
[52] U.S. Cl. .................................... 252/49.8; 260/983
[58] Field of Search ...................... 260/983; 252/49.8; 184/1 E

[56] References Cited

U.S. PATENT DOCUMENTS

| | | | |
|---|---|---|---|
| 2,957,931 | 10/1960 | Hamilton et al. | 252/49.8 X |
| 2,963,437 | 12/1960 | Ries | 252/49.8 |
| 3,019,249 | 1/1962 | Gunderloy | 260/978 X |
| 3,496,104 | 2/1970 | Shimada et al. | 252/49.8 X |
| 3,583,915 | 6/1971 | Myers | 252/49.8 X |
| 3,600,470 | 8/1971 | Lewis | 252/49.8 X |
| 3,714,043 | 1/1973 | Clark | 252/49.8 X |

Primary Examiner—Delbert E. Gantz
Assistant Examiner—Andrew Metz
Attorney, Agent, or Firm—Charles A. Huggett; Raymond W. Barclay; Howard M. Flournoy

[57] ABSTRACT

Aryl phosphonates of high purity, prepared by heating the corresponding aryl di-t-alkyl phosphite in the presence of a heterogeneous acidic reticular resin catalyst, are incorporated into various lubricant compositions to provide such compositions with improved antiwear properties.

14 Claims, No Drawings

PROCESS OF PREPARING MONOARYL PHOSPHONATES AND LUBRICANT COMPOSITIONS CONTAINING SAME

CROSS-REFERENCE TO RELATED APPLICATIONS

This is a divisional of U.S. Ser. No. 717,815 filed Aug. 26, 1976 of same title and now U.S. Pat. No. 4,092,254.

BACKGROUND OF THE INVENTION

1. Field of the Invention

This invention relates to a process for the preparation of monoaryl phosphonates, useful as antiwear additives, a method for reducing wear between moving metal surfaces in contact with a lubricant composition containing an effective amount of said antiwear additive and to lubricant compositions comprising a major proportion of an oil of lubricating viscosity or grease prepared therefrom containing a minor amount of said antiwear additive.

2. Description of the Prior Art

Monoaryl phosphonates have heretofore been prepared, as described in U.S. Pat. No. 3,019,249, by the reaction of phosphorous acid with triaryl phosphites in accordance with the general equation:

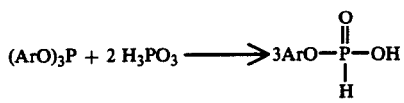

One disadvantage to this method is that monoaryl phosphonates so produced are difficult to purify and the product is usually contaminated with one of the reactants. Also, phosphorous acid is hygroscopic, and accidentally-absorbed water in the phosphorous acid reactant will hydrolyze part of the product monoaryl phosphonate to phosphorous acid and the corresponding phenol.

Another method for preparing monoaryl phosphonates is described in Houben Weyl, "Methoden der Organischen Chemie", edited by Eugen Müller, Georg Thieme Verlag, Stuttgart, 1964, Vol. 12, part 2, page 6. This method involves hydrolysis of the corresponding aryl-phosphorodichloridite in accordance with the following general equation:

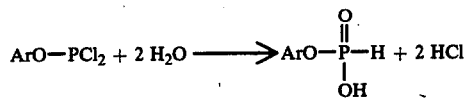

As stated in Houben Weyl, the product is unstable in the reaction medium and usually hydrolyzes extensively before it can be isolated.

The method in accordance with this invention provides a general catalytic synthesis of monoaryl phosphonates which may be accomplished in the absence of water or other hydroxylic impurities and which affords a substantially pure monoaryl phosphonate product which is virtually free of other phosphorous-containing impurities and which is capable of easy separation from the catalyst employed.

SUMMARY OF THE INVENTION

This application is directed to a process wherein monoaryl phosphonates are prepared by heating the corresponding aryl-di-t-alkyl phosphite in the presence of heterogeneous acid catalyst on an inert particulate matrix. This application is further directed to lubricant compositions comprising oils of lubricating viscosity, greases and functional oils or fluids prepared therefrom containing a minor amount sufficient to improve the antiwear properties thereof of said monoaryl phosphonate.

Further, this application in one of its aspects is directed to a process for the preparation of monoaryl phosphonates of the following general structure:

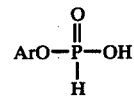

wherein Ar is selected from the group consisting of phenyl, alkyl phenyl, halophenyl, haloalkyl phenyl, ketoalkyl phenyl, alkoxy phenyl, carbalkoxy phenyl, naphthyl, alkyl naphthyl, haloalkyl naphthyl, ketoalkyl naphthyl, alkoxy naphthyl, and carbalkoxy naphthyl; said alkyl and alkoxy substituents thereof having from 1 to about 30 carbon atoms, comprising heating the corresponding aryl-di-t-alkyl phosphite at a temperature of from about 60°–150° C. in the presence of a heterogeneous acid cation exchange resin catalyst and recovering the desired monoaryl phosphonate.

In a further aspect, this application is directed to a method for reducing wear between moving metal surfaces, e.g., steel-on-steel; which comprises introducing between said surfaces a lubricant composition comprising a major amount of an oil of lubricating viscosity or a grease prepared therefrom and a minor amount sufficient to improve the antiwear properties of said composition of a monoaryl phosphonate of the following general structure:

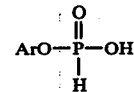

wherein Ar is selected from the group consisting of phenyl, alkyl phenyl, halophenyl, haloalkyl phenyl, ketoalkyl phenyl, alkoxy phenyl, carbalkoxy phenyl, naphthyl, alkyl naphthyl, haloalkyl naphthyl, ketoalkyl naphthyl, alkoxy naphthyl, and carbalkoxy naphthyl; said alkyl and alkoxy substituents thereof having from 1 to 30 carbon atoms.

Ar is preferably selected from the group consisting of phenyl, alkyl phenyl, halophenyl, haloalkyl phenyl, ketoalkyl phenyl, alkoxy phenyl, and carbalkoxy phenyl and more preferably alkylphenyl. It is understood that halo includes chloro-, fluoro-, bromo- and iodophenyl.

DESCRIPTION OF SPECIFIC EMBODIMENTS

In general, this application in its preferred embodiments, contemplates lubricant compositions containing the hereindescribed aryl phosphonates, i.e., lubricant compositions comprising a major amount of an oil of lubricating viscosity greases prepared therefrom and various functional fluids, or special purpose oils thereof, such as transmission or hydraulic fluids and a minor amount sufficient to improve the antiwear properties of the aforementioned lubricant compositions of a monoaryl phosphonate as above described. Generally, for most applications, the antiwear additive is present in an amount from about 0.05 to about 5%, by weight of the total composition, and preferably in an amount from about 0.1 to about 2%, by weight although the additive can be present in an amount up to about 10% by weight. The contemplated lubricant compositions may comprise any materials that normally exhibit insufficient antiwear properties. Especially suitable for use with the antiwear additives of this invention are liquid hydrocarbon oils boiling within the range from about 75° F. to about 1,000° F. Lubricant oils, improved in accordance with the present invention, may be of any suitable lubricating viscosity range from about 45 SSU at 100° F., to about 6,000 SSU at 100° F. and, preferably, from about 50 to 250 SSU at 210° F. Oils having viscosity indexes from about 70 to about 95 are preferred. The average molecular weights of these oils may range from about 250 to about 800. In general, the lubricant may comprise any mineral or synthetic oil of lubricating viscosity.

In instances where synthetic oils are desired in preference to mineral oils they may be employed alone or in combination therewith, and also used as the vehicle for grease compositions. Typical synthetic lubricants include polyisobutylene, polybutenes, hydrogenated polydecenes, polypropylene glycol, polyethylene glycol, trimethylol propane esters, neopentyl and pentaerythritol esters, di(2-ethyl hexyl) sebacate, di(2-ethyl hexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, phenoxy phenylethers, etc.

As hereinbefore indicated, the aforementioned additives may be incorporated as antiwear agents in grease compositions. When high temperature stability is not a requirement of the finished grease, mineral oils having a viscosity of at least 40 SSU at 100° F., and particularly those falling within the range from about 60 SSU to about 6,000 SSU at 100° F. may be employed. The lubricating compositions of the improved greases of the present invention, containing the above-described additives, are combined with a grease-forming quantity of a thickening agent. For this purpose, a wide variety of materials can be dispersed in the lubricating vehicle in grease-forming quantities in such degree as to impart to the resulting grease composition the desired consistency. Exemplary of the thickening agents that may be employed in the grease formulation are non-soap thickeners, such as surface-modified clays and silicas, aryl ureas, calcium complexes and similar materials. In general, grease thickeners are employed which do not melt and dissolve when used at the required temperature within a particular environment; however, in all other respects, any material which is normally employed for thickening or gelling oleaginous fluids or forming greases may be used in the present invention.

Generally, the catalysts contemplated for use in the novel process embodied herein as mentioned heretofore are heterogeneous acid catalysts on an inert matrix. Particularly suitable are such catalysts as macroreticular acid cation exchange resin catalysts, such as Amberlyst-15 which are characterized by substantial porosity, high surface area, low surface acid concentration, usually less than about 0.5 milliequivalents of hydrogen ion per square meter surface area.

The macroreticular resins utilized in the process of this invention are characterized by the presence of acid functional groups and a structure having a high degree of true porosity while possessing rigidity and being subject to minimum volume change when immersed or removed from solvents or solutions.

The macroreticular acid ion exchange resin employed is typified by the presence of sulfonic acid groups, e.g., the sulfonated styrene-divinylbenzene copolymer exchange resins such as those commercially available as Amberlyst-15, Amberlyst XN-1005, Amberlyst XN-1010, Amberlyst XN-1011, Amberlyst XN-1008 and Amberlite 200. The properties of these macroreticular resins, along with Amberlite IR-120H, a typical microreticular resin are shown below:

| Resin | Macroreticular | | | | | | Microretricular |
|---|---|---|---|---|---|---|---|
| | Amberlyst-15 | Amberlyst-XN-1005 | Amberlyst-XN-1010 | Amberlyst-XN-1011 | Amberlyst-XN-1008 | Amberlite-200 | Amberlite-IR-120H |
| Skeletal Structure | Styrene-DVB | do. | do. | do. | do. | do. | do. |
| Ionic Functionality | $RSO_3H$ | do. | do. | do. | do. | do. | do. |
| Hydrogen Ion Concentration meq/g dry (Exchange Capacity) | 4.9 | 3.4 | 3.3 | 4.2 | 4.5 | 4.3 | 5.0 |
| Porosity, % | 32 | 42 | 47 | 24 | — | — | 1.8 |
| Avg. Pore Diameter, A° | 200–600 | 80–90 | 40–50 | — | 400–800 | — | — |
| Cross-linkage | ~20 | — | — | — | — | ~20 | 8 |
| Surface Area $^2$/g dry | 40–50 | 100–200 | 550–600 | 28 | 30–40 | 40–50 | <0.1 |
| Surface Acid Concentration meq $H+/m^2$ S.A. | 0.102 | 0.031 | 0.006 | 0.150 | 0.129 | 0.096 | >50 |

The subject monoaryl phosphonates additives [3] are conveniently prepared as indicated below by thermal cleavage, at a temperature of about 60°–150° C. and preferably from about 80°–130° C., of an aryl-di-t-alkyl phosphite [1], e.g., an aryl-di-t-butyl or aryl-di-t-amyl phosphite followed by acid-catalyzed elimination of a second molecule of, for example, isobutylene from the intermediate aryl-alkyl phosphonate [2].

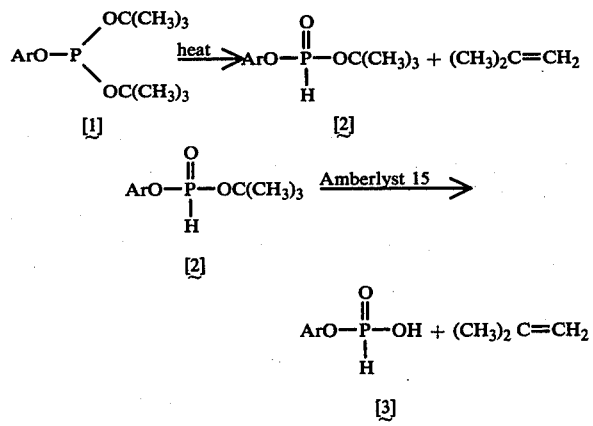

It is usually convenient to conduct the thermal step and the acid-catalyzed step at the same time. In order to get convenient reaction rates, it is also desirable to use a phosphite ester of a tertiary alcohol such as tert-butyl alcohol or tert-amyl alcohol. However, any suitable tert-$C_4$-$C_{30}$ alcohol may be conveniently used.

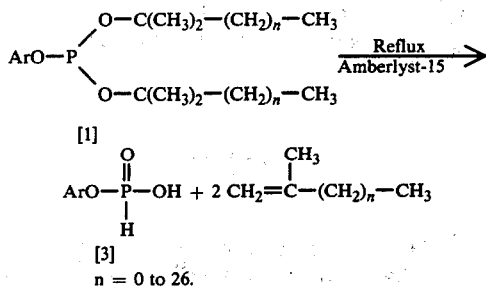

$n = 0$ to $26$.

The aryl group can be phenyl, alkyl phenyl, halophenyl, etc. as hereinbefore described; said alkyl and alkoxy substituents thereof having from 1 to about 30 carbon atoms with the alkyl group of said phosphite containing from 4 to about 30 carbon atoms and being preferably butyl or amyl.

The following provides examples of the subject monoaryl phosphonates and antiwear data showing their utility. It will be understood that it is not intended that the invention be limited to the particular antiwear additives as described, and that various modifications thereof can be employed and will be readily apparent to those skilled in the art.

EXAMPLE 1

Preparation of 4-n-Nonylphenyl phosphonate

A solution of 4-n-nonylphenol (0.04 mol, 8.8 g) and N,N-diethylaniline (0.04 mol, 5.96 g) in 75 ml hexane was added dropwise with stirring to excess phosphorous trichloride (0.4 mol, 55 g) in 100 ml hexane. The mixture was stirred 1 hr. at room temperature and filtered. After removal of solvent and excess $PCL_3$ by vacuum distillation, 11.95 g (0.0372 mol) of 4-n-nonylphenyl phosphorodichlorodite was obtained. A hexane solution (100 ml) of t-butanol (0.0744 mol, 5.51 g) and N,N-diethylaniline (0.744 mol, 11.09 g) was added dropwise to a solution of the phosphorodichlorodite in 50 ml of hexane. Upon completion of the addition, the solution was refluxed 30 minutes, filtered and evaporated under vacuum to give a residue of 4-n-nonylphenyl-di-t-butyl phosphite (0.0332 mol, 13.14 g). The phosphite was heated at reflux in 50 ml toluene containing a suspension of Amberlyst 15 (2 g) resin for 90 min. The Amberlyst 15 was removed by filtration, and solvent was removed in vacuo to give 8.69 g (0.0306 mol) 4-n-nonylphenyl phosphonate as a colorless oil. The following confirms the product structure: IR (Infrared) 3600 cm-1 (OH); 31p NMR (nuclear magnetic resonance) ($C_5D_5N$)$\delta$-0.35 (d,l,J=636); $^1$H NMR ($CDCl_3$)$\delta$0.9–1.3 (t, 3 + env. 14 alkyl), 2.5 (t, 2 alkyl, J 7Hz), 7.03 (4 arom), 7.28 (d, 0.8, J=710), 11.65 (s,0.9, OH). Ammonium salt m. 133°–135°. Anal. Calcd. for $C_{15}H_{28}O_3NP$: C, 59.78; H, 9.36; O, 15.93; N, 4.65; P, 10.29. Found: C, 59.60; H, 9.86; N, 4.74; P, 10.58.

EXAMPLE 2

4-n-Nonylphenyl phosphonate is prepared according to the procedure of Example 1, except that 4-n-nonylphenyl-di-t-amyl phosphite is used.

Example 1 illustrates that the method of this invention provides essentially pure mononoylphenyl phosphonate, free of other phosphorus-containing impurities. Only a minute amount of di(nonylphenyl) phosphonate was present in the product due to an impurity in the nonylphenyl phosphorodichlorodite from which the nonylphenyl-di-t-butyl phosphite was prepared. No other phosphorous impurities were present.

The additives were tested for antiwear activity using the Four Ball Wear Test, disclosed in U.S. Pat. No. 3,423,316. In general, in this test three steel balls of SAE 52100 steel are held in a ball cup. A fourth ball positioned on a rotatable vertical axis is brought into contact with the three balls and is rotated against them. The force with which the fourth is held against the three stationary balls may be varied according to a desired load. The test lubricant is added to the ball cup and acts as a lubricant for the rotation. At the end of the test, the steel balls are investigated for wear scar; the extent of scarring represents the effectiveness of the lubricant as an antiwear agent. Results are also reported as wear rates in volume of wear per unit sliding distance per kilogram load. The lower the wear rate, the more effective the lubricant as an antiwear agent. The base stock oil employed in accordance with the test results shown in the table comprised a 150 SSU at 210° F. solvent-refined paraffinic bright stock lubricating oil. The additive was tested at a concentration of 0.5% wt. standard conditions of 40 Kg load, 600 rpm, and 30 minutes test time were employed at 200° F.

TABLE

| | (Steel - on - Steel) | |
|---|---|---|
| Additive | Wear Scar Diameter, mm | Wear Rate $\times 10^{12}$ cc/cm-Kg |
| None | 0.6858 | 4.60 |
| Example 1 | 0.3885 | 0.282 |

As will be apparent from the data of the foregoing Table 1, the lubricant composition of the present invention exhibit highly improved antiwear properties, as evidenced by the indicated comparative data with respect to wear scar diameter and wear rate.

While the present invention has been described with reference to preferred compositions and modifications thereof, it will be apparent to those skilled in the art that departure from the preferred embodiments can be effectively made and are within the scope of the specification.

We claim:

1. A process for the preparation of monoaryl phosphonates of the following general structure:

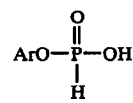

wherein Ar is selected from the group consisting of phenyl, alkyl phenyl, halophenyl, haloalkyl phenyl, ketoalkyl phenyl, alkoxy phenyl, carbalkoxy phenyl, naphthyl, alkyl naphthyl, halonaphthyl, haloalkyl naphthyl, ketoalkyl naphthyl, alkoxy naphthyl, and carbalkoxy naphthyl, said alkyl and alkoxy substituents thereof having from 1 to about 30 carbon atoms, comprising heating the corresponding aryl di - t - $C_4$-$C_{30}$ alkyl phosphite at a temperature of from about 60°-150° C. in the presence of a heterogeneous acid cation exchange resin catalyst and recovering the desired monoaryl phosphonate.

2. The process of claim 1 wherein Ar is selected from the group consisting of phenyl, alkyl phenyl, halophenyl, haloalkyl phenyl, ketoalkyl phenyl, alkoxy phenyl and carbalkoxy phenyl.

3. The process of claim 2 wherein Ar is alkylphenyl.

4. The process of claim 3 wherein the monoaryl phosphonate is 4-n-nonylphenyl phosphonate.

5. The process of claim 1 wherein the alkyl group of said phosphite is butyl or amyl.

6. The process of claim 1 wherein said catalyst exchange resin consists essentially of a macroreticular acid cation exchange resin characterized by a water content between about 0.5 and about 20 weight percent, a surface area of at least 30 square meters per gram and a surface acid concentration of between 0.001 and about 0.5 milliequivalents of hydrogen ion per square meter surface area.

7. The process of claim 1 wherein said temperature is between about 60°-130° C.

8. The process of claim 1 wherein said surface acid concentration is between 0.001 and 0.2 milliequivalents of hydrogen ion per square meter surface area.

9. The process of claim 1 wherein said resin consists essentially of a macroreticular sulfonic acid cation exchange resin.

10. A method for reducing wear between moving metal surfaces which comprises introducing between said surfaces a lubricant composition comprising a major amount of an oil of lubricating viscosity or a grease prepared therefrom and a minor amount sufficient to improve the antiwear properties of said composition of a monoaryl phosphonate of the following general structure:

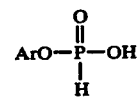

wherein Ar is selected from the group consisting of phenyl, alkyl phenyl, halophenyl, haloalkyl phenyl, ketoalkyl phenyl, alkoxyphenyl, carbalkoxy phenyl, naphthyl, alkyl naphthyl, halonaphthyl, haloalkyl naphthyl, ketoalkyl naphthyl, alkoxy naphthyl, and carbalkoxy naphthyl said alkyl and alkoxy substituents thereof having from 1 to about 30 carbon atoms.

11. The method of claim 10 wherein the monoaryl phosphonate is present in an amount from about 0.5 to about 5% by weight of the total composition.

12. The method of claim 11 wherein the monoaryl phosphonate is present in an amount from about 0.1 to about 2% by weight.

13. The method of claim 11 wherein said moving metal surfaces are steel-on-steel.

14. The method of claim 10 wherein the monoaryl phosphonate is 4-n-nonylphenyl phosphonate.

* * * * *